United States Patent [19]

Zibelin

[11] Patent Number: 4,509,517
[45] Date of Patent: Apr. 9, 1985

[54] KIDNEY STONE INSTRUMENT

[76] Inventor: Henry S. Zibelin, 1423 26th St. NW., Winter Haven, Fla. 33880

[21] Appl. No.: 430,353

[22] Filed: Sep. 30, 1982

[51] Int. Cl.³ .............................................. A61B 17/00
[52] U.S. Cl. .................................. 128/319; 128/321; 128/328; 128/346; 81/111
[58] Field of Search .............. 128/356, 321, 345, 328, 128/346, 319, 303 R, 322; 81/111, 112

[56] References Cited

U.S. PATENT DOCUMENTS 2,518,994  8/1950  Miller .................................. 128/321
3,868,956  3/1975  Alfidi et al. ..................... 128/1 R X

FOREIGN PATENT DOCUMENTS 940761  7/1982  U.S.S.R. .............................. 128/328

*Primary Examiner*—Michael H. Thaler
*Attorney, Agent, or Firm*—Fred Philpitt

[57] ABSTRACT

The present invention pertains to an instrument for insertion into the body which can grasp and crush or grasp and remove kidney stones, the jaws of this instrument being moved together or apart by means of a shape memory metal alloy.

4 Claims, 11 Drawing Figures

KIDNEY STONE INSTRUMENT

A number of different types of instruments have been proposed for the removal of kidney stones. U.S. Pat. Nos. 3,334,630 and 3,827,437 are illustrative of such instruments. Mose of these instruments involve rather complex mechanical arrangements and are not as light weight as desired because of the components of the device and the strength needed in each component.

The present invention provides a simple light weight instrument that can grasp and/or crush kidney stones that are located inside the body. In particular, the present invention pertains to an instrument for the grasping and/or crushing of kidney stones that uses as one component a strip or wire of a shape memory alloy, especially Nitinol. There is a host of alloys, called shape memory alloys. When an alloy of this group is annealed at a very high temperature (typically 1000° C. or above) in a given shape, the shape is fixed permanently unless it is annealed once again. If the alloy is cooled down below a certain temperature (typically 45° C.–80° C.) called a transition temperature, it becomes quite weak mechanically and can thus be deformed relatively easily. After the deformation, if the temperature of the alloy is raised above the transition temperature, it recovers its originally fixed shape by changing phase of its crystal structure. Both the annealing temperature and the transition temperature depend on alloys.

An example of the shape memory alloy in Nitinol. This is made of nickel, titanium, a small amount of iron and a small amount of nitrogen. In metallurgical terms, this can be expressed as:

Ni(40–52)Ti(0–0.1)Fe-(0–0.1)N

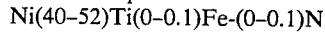

Where the numbers in parentheses indicate ranges of weight percentages of each following element. Other examples of shape memory alloys are:

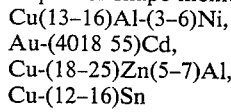

Cu(13–16)Al-(3–6)Ni,
Au-(4018 55)Cd,
Cu-(18–25)Zn(5–7)Al,
Cu-(12–16)Sn and other alloys such as Ag-Cd, Ag-Cd, Ag-Zn, Cu-Al, Cu-Zn, Fe-Bem, Fe-Pt, In Tl, Nb-Ti, Ni-Al, etc.

The present invention will be particularly described with reference to Nitinol, but it will be appreciated that similarly behaving materials may be used instead.

In recent years an alloy of nickel and titanium of particular stoichiometric composition has been developed that has memory of particular stable dimensions and a martensitic critical temperature at which the mechanical memory is activated. A length of wire of the alloy has the following characteristics: when tensile stress is applied to a length of the wire of stable dimension sufficient to stretch the wire up to a near 10 percent of its length but not exceeding a predetermined maximum for the alloy and then the tensile stress is removed. The wire is dimensionally quiescent indefinitely. At its stretched length provided that its temperature is not elevated to a martensitic critical temperature. When the temperature of the stretched wire is elevated to the martensitic critical temperature of the alloy, the wire dimension is substantially instantly restored to that prior to elongation and during the restoration the wire exhibits substantial tensile force. The rate of restoration can be varied by varying the rate at which the wire is heated when it is at its critical temperature. When the wire restores to its prestretched length it exhibits contraction force several times the tensile force required for stretching the wire at lower temperature. The martensitic critical temperature is related to the stoichiometric composition of the alloy. Alloys exhibiting the above property are described in U.S. Pat. No. 3,174,851 to Buehler; U.S. Pat. No. 3,403,238 to Buehler; and the Wire Journal of 1969—"55-Nitinol, Unique Wire Alloy With a Memory" by W. J. Buehler and W. B. Cross.

The alloy 55-Nitinol includes titanium and nickel and has a particular martensitic critical temperature depending on composition and which tempeature ranges upwardly from about 140° F. A length of wire of 55-Nitinol, 0.020 inches in diameter, stretched to about 108 percent of its prestretched length, restores to its prestretched length when elevated to its martensitic critical temperature and exerts a tensile force that can be over 30 pounds. The wire has very little mass. If one end of the wire is fixed, the other end moves toward the fixed end during contraction with a peak speed on the order of 1,000 feet per second. The contraction speed depends upon the characteristic of the specific alloy and the rate at which the material is heated at its critical temperature.

In the following discussion and in the claims "critical temperature" is used synonymously with transition temperature as these terms are used in connection with shape memory metals.

THE PRESENT INVENTION

Considered from one standpoint the present invention involves an instrument for the removal of kidney stones that includes the combination of (a) a kidney stone crusher means comprising at least one pair of opposed jaw members, and
(b) means for alternately moving said jaw members toward each other and away from each other, said means including
  (1) at least one annular member that surrounds at least a portion of the jaw members and which is adapted to move for a limited distance parallel to the longitudinal axis of said jaw members,
  (2) at least one strip of Nitinol having one end attached to said longitudinally movable annular member and the other end attached to a portion of the instrument that does not move axially with respect to said jaw members, and
  (3) mechanical pressure means for maintaining sufficient pressure on said nitinol strip when said strip is below its critical temperature so that said strip will be deformed out of a planar disposition, but said sufficient pressure being inadequate to maintain said Nitinol strip in a deformed position when the nitinol is heated above its critical temperature, whereby, said jaws will be maintained in an open position to receive kidney stones when said nitinol strip is below said critical temperature and said jaws will move from an open to a more closed position to grasp kidney stones when said nitinol strip is above said critical temperature.

Several emdobiments of the invention are illustrated by the drawings wherein.

Figure 1:
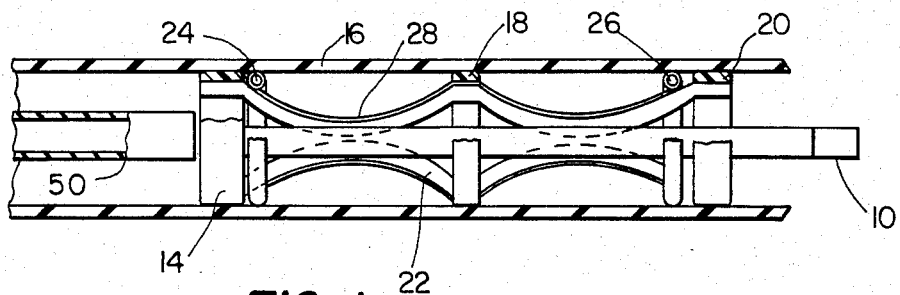
FIG. 1 is a top sectional view of a first embodiment of my invention in a jaws open position.

Referring now to the drawings, FIGS. 1–4 show a first embodiment of my invention. Jaw members 10 and 12 are seen to consist of two toothed outer jaw sections that can move toward and away from each other and two inner ends that are anchored to a ring 14. Ring 14 is preferably fastened to suitable flexible tubing 16. The jaw members 10 and 12 are also surrounded by rings 18 and 20, neither of which is anchored to the tubing 16 or the jaw members 10 and 12. Rings 18 and 20 are able to move longitudinally for a limited distance within tubing 16.

At least one and preferably at least two Nitinol strips 22 interconnect rings 14, 18 and 20, the ends of strips 22 being attached to rings 14 and 20 by any suitable means.

Rings 24 and 26 are positioned annularly around the strips 22 and the jaw members 10 and 12 as shown. Rings 24 and 26 in conjunction with ring 18 serve to support a spring strip 28, which is shaped so that it will exert a deformation pressure against the Nitinol strips 22 so as to deform strip 22 out of a purely linear or planar position and into an arcuate position, as shown, when the Nitinol is below its critical temperature.

The spring strip 28, made of steel or other metal or perhaps a suitable plastic material, is secured to the rings 24 and 26 by any suitable means (e.g. welding, looping, etc.) and also to or through the intermediate ring 18. The spring strip 28 is preferably not bonded to the length of Nitinol. The Nitinol strips 22 and strip 28 are preferably held in ring 18 by a pin or an inner retaining ring.

Figure 2:
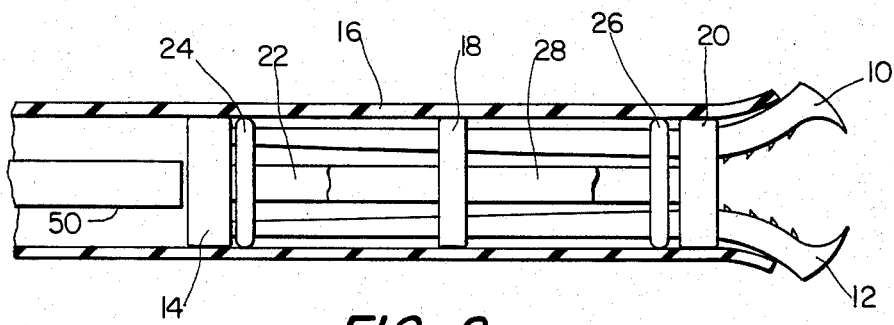
FIG. 2 is a side sectional view of FIG. 1.
Figure 3:
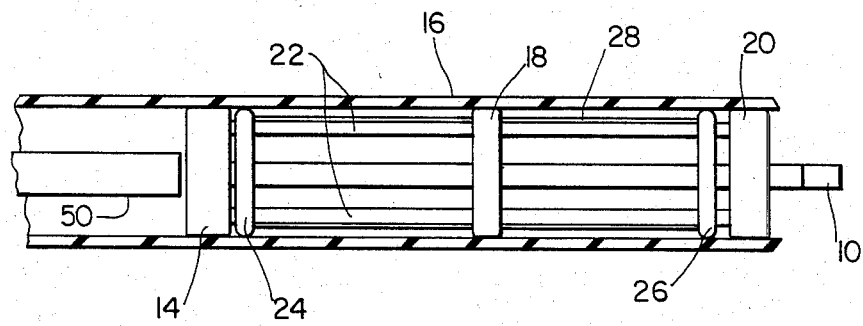
FIG. 3 is a top section view of a first embodiment of my invention in a jaws closed position.

When the critical temperature is exceeded in the vicinity of the instrument the Nitinol strip 22 will snap back to a straight or planar position that is best shown in FIG. 3 and this snapping back or retractive force is sufficiently great that it overcomes the inward deforming pressure of the spring strips 28. When the Nitinol strip 22 changes from the position shown in FIG. 1 to that shown in FIG. 3, because of the transition from "below critical temperature" to "above critical temperature", the toothed jaw members 10 and 12 will change from the position shown in FIG. 2 to that shown in FIG. 4. When the temperature of the instrument is reduced below the "critical temperature" again the jaws will return to the position shown in FIGS. 1 and 2 since the deforming pressure of the steel strips will prevail.

The temperature of the instrument can be changed from below critical to above critical in a number of different ways. One way which is simple and quick is to introduce a fluid of the desired temperature thru conduit 50, and such fluid will quickly influence each part of the instrument that it comes in contact with. The introduction of a fluid to achieve temperature change also has the advantage that it can be a medium for carrying away kidney stone fragments after they are crushed by the jaw members.

Considered from another standpoint the present invention involves an instrument for the removal of kidney stones that includes the combination of (a) a kidney stone grasping means comprising at least one pair of opposed jaw members that are mounted in a support which is mounted for axial movement in a tube, (b) means for alternately moving said jaw members toward each other and away from each other, said means including
  (1) a first resilient means for urging the toothed sections of said jaw members apart in an "open" position,
  (2) at least one length of Nitinol having one end attached to said axially movable jaw member support and the other end attached to a spaced apart fixed point on the tube in which said jaw members are mounted,
  (3) mechanical pressure means for maintaining sufficient pressure on said length of Nitinol when said length is below its critical temperature so that said length of Nitinol will be stretched in a lengthwise direction, but said sufficient pressure being inadequate to maintain said length of Nitinol in a stretched position when the Nitinol is heated above its critical temperature, whereby said jaws will be maintained in an open position to receive kidney stones when said length of Nitinol is below said critical temperature and said jaws will move from an open to a closed position to grasp and/or crush kidney stones when said length of Nitinol is above said critical temperature.

Figure 5:
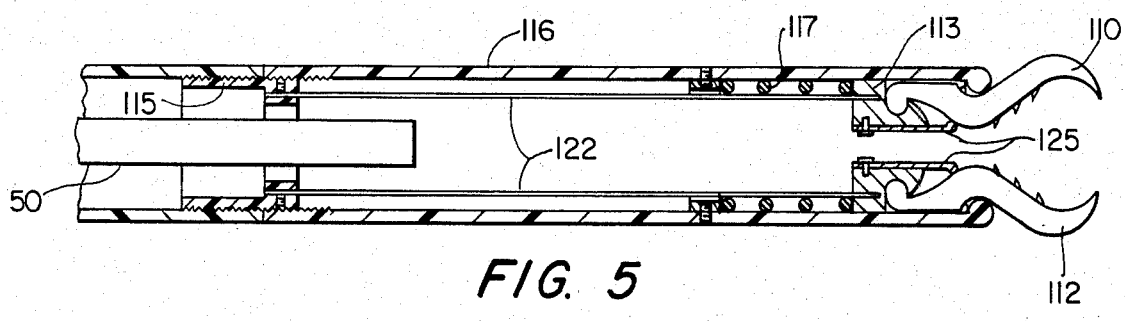
FIG. 5 is a side sectional view of a second embodiment of my invention in a jaws open position.
Figure 6:
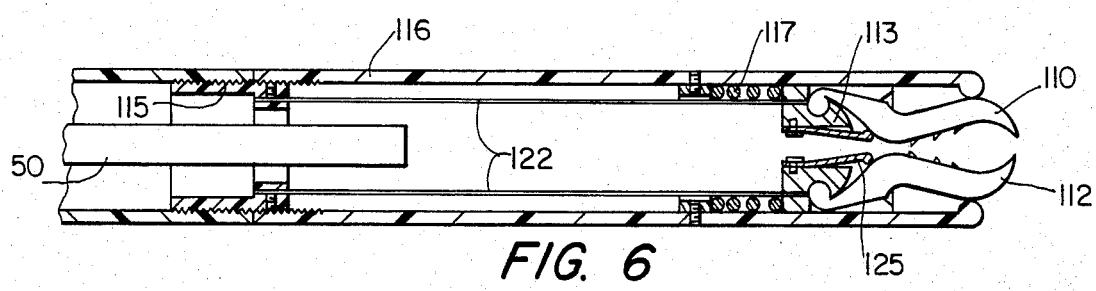
FIG. 6 is a side sectional view of a second embodiment of my invention in a jaws closed position.

Referring now to the drawings, FIGS. 5 and 6 show a second preferred embodiment of my invention. Jaw members 110 and 112 are seen to consist of two toothed outer jaw sections that can move toward and away from each other, the inner ends of these jaw members being pivotally mounted in a support member 113 that is axially movable within a rigid tube 116. An anchor member 115 is fixedly located a spaced distance away on the interior of tube 116 and the support member 113 is connected to the anchor member 115 by means of one or more Nitinol strips or wires 122. First resilient mea such as leaf springs 125 normally urge the jaws 110 and 112 apart (see FIG. 5). However, when the temperature of the Nitinol strips or wires 122 increases from below the critical temperature to above the critical temperature, the length of the Nitinol strips or wires will decrease from their extended postion (FIG. 5) to their retracted position (FIG. 6)—and when this occurs the jaw members 110 and 112 will change as is shown in FIGS. 5 and 6. The retractive force generated by the change in temperature from below the critical temperature to above the crtical temperature is sufficiently great to overcome the force of spring 117, which is always trying to push the support member 113 and jaw members 110 and 112 to the position shown in FIG. 5. The spring 117 thus becomes compressed, as is shown in FIG. 6 and as the jaw members 110 and 112 move to the position shown in FIG. 6 the jaw members overcome the force of the leaf springs that would normally urge the jaw members apart.

Figure 7:
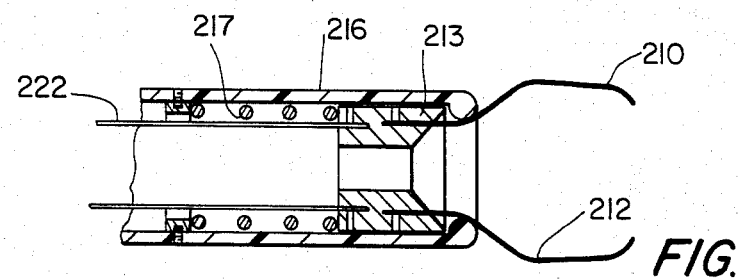
FIGS. 7 and 8 are sectional views of a third embodiment of my invention.
Figure 8:
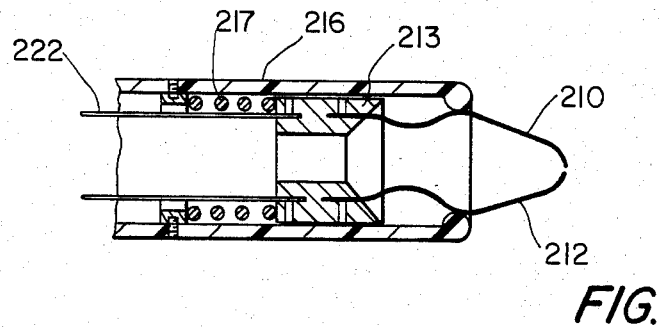
Figure 9:
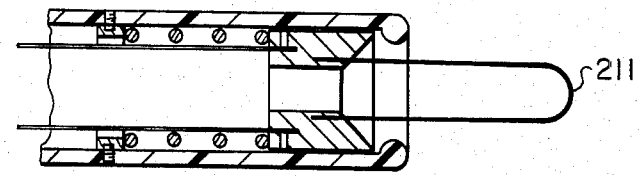
FIG. 9 is a sectional view of a fourth embodiment of my invention.

FIGS. 7, 8 and 9 show other embodiments of my inventive concept which are very similar to the embodiments of FIGS. 5 and 6 except that the jaw members have been replaced with either cooperating retrieving arms 210 and 212 made of wire or the like, or with a single loop of wire 211. The embodiments of FIGS. 7 and 8 do not employ leaf springs because the natural resiliency of these shaped wires biases them to the open position shown in FIG. 7.

Figure 4:
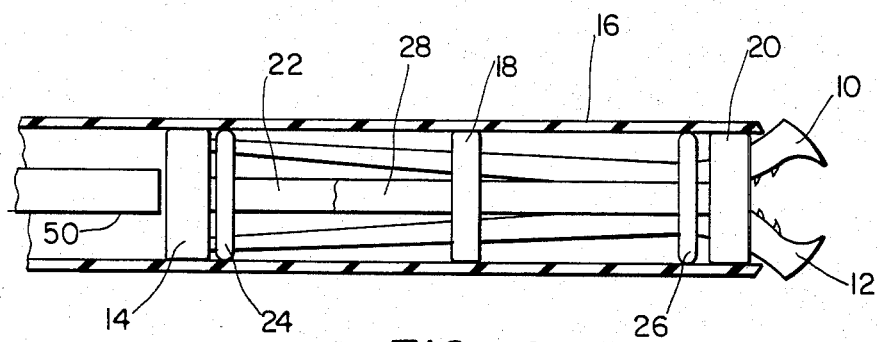
FIG. 4 is a side sectional view of FIG. 3.

It will be seen that with the instrument of this invention, an area of the body containing a kidney stone may be approached with the jaws in the position shown in FIG. 4, the jaws opened as in FIG. 2 so that the jaws can grasp the stone, and the jaws then closed (as in FIG. 4) so as to grasp and/or crush the kidney stone. It would also be possible to approach the kidney stone with the jaws in the FIG. 2 position and to thereafter grasp and/or crush the stone by moving the jaws to the position shown in FIG. 4. As indicated, the opening or closing of the jaw members of this invention can be simply achieved by introducing water of the appropriate temperature (i.e. at a temperature either below or above the critical (or transition) temperature of the shape memory alloy. Opening or closing is thus simple and quick.

Figure 10:
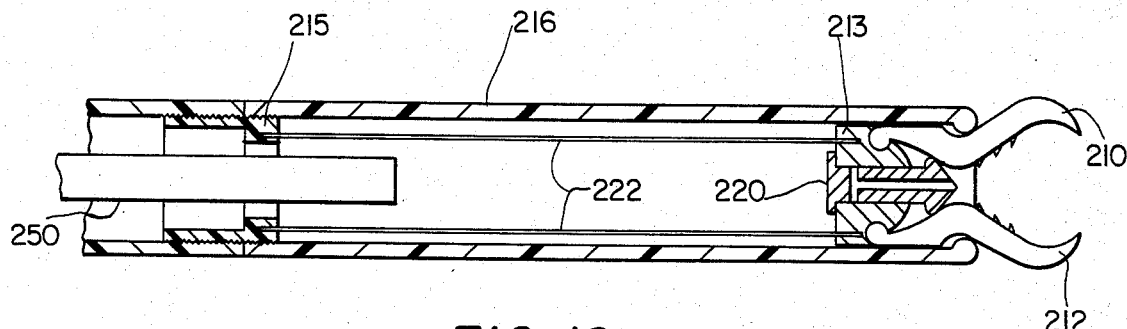
FIGS. 10 and 11 are sectional views of a fifth embodiment of my invention.
Figure 11:
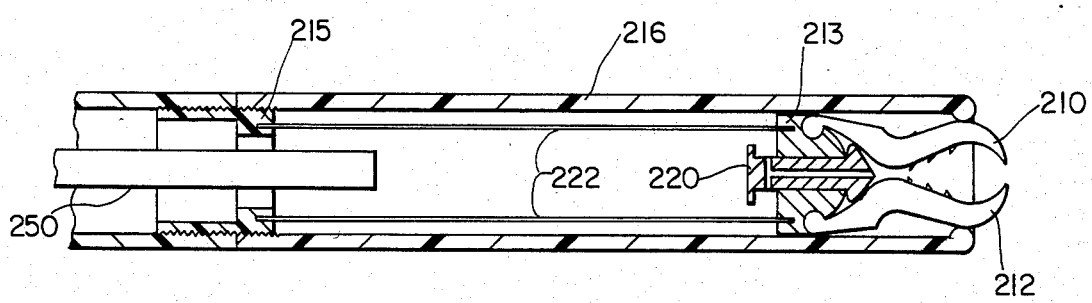

In accordance with another embodiment of my invention, illustrated in FIGS. 10 and 11, members 210 and 212 are seen to consist of two toothed outer jaw sections that can move toward and away from each other, the inner ends of these jaw members being pivotally mounted in a jaw support member 213 that is axially moveable within a rigid tube 216. An anchor member 215 is fixedly located a spaced distance away on the interior of tube 216 and the support member 213 is connected to the anchor member 215 by means of one or more Nitinol strips or wires 222. When fluid having a temperature below the critical temperature of the Nitinol is introduced thru tube 250 the check valve 220 will be forced under fluid pressure to the right as is shown in FIG. 10. However, when the temperature of the fluid introduced thru 250 is increased above the critical temperature of the Nitinol, the length of the Nitinol strips or wires 222 will quickly decrease from that shown in FIG. 10 to that shown in FIG. 11—and when this occurs the jaw members 210 and 212 will move toward each other because the support member will be pulled to the left by the contracting strips or wires 222. When the jaws 210 and 212 close toward each other the inner portions thereof will squeeze the right end of the check valve to the left with respect to support member 213, as is seen in FIG. 11, and in this position the T-shaped bleeder passageway in check valve 220 will open so that the rightward fluid pressure against the piston-like side of check valve is reduced, which means there is less fluid pressure acting against the contractive force of the strips or wires 222. When the temperature of the fluid is reduced again below the critical temperature of the Nitinol, the strips or wires 222 lengthen, the jaws diverge so that they no longer exert a squeezing force on the check valve, and the rightward pressure of the fluid will move the check valve back to the position shown in FIG. 10.

I claim:

1. An instrument for the removal of kidney stones that includes the combination of
   (a) a kidney stone grasping means comprising at least one pair of opposed jaw members that are mounted in a support which is mounted for axial movement in a tube,
   (b) means for alternately moving said jaw members toward each other and away from each other, said means including
      (1) a first resilient means for urging the toothed sections of said jaw members apart in an "open" position,
      (2) at least one length of Nitinol having one end attached to said axially movable jaw member support and the other end attached to a spaced apart fixed point on the tube in which said jaw members are mounted,
      (3) mechanical pressure means for maintaining sufficient pressure on said length of Nitinol when said length is below its critical temperature condition so that said length of Nitinol will be stretched in a lengthwise direction, but said sufficient pressure being inadequate to maintain said length of Nitinol in a stretched position when the Nitinol is heated above its critical temperature, and
      (4) means to control the temperature of said Nitinol,
   whereby said jaws will be maintained in an open position to receive kidney stones when said length of Nitinol is below said critical temperature and said jaws will move from an open to a closed position to grasp and/or crush kidney stones when said length of Nitinol is above said critical temperature.

2. An instrument according to claim 1 wherein said means for controlling the temperature of the Nitinol is a fluid of the desired temperature.

3. An instrument according to claim 1 wherein said mechanical pressure means is a spring.

4. An instrument according to claim 2 wherein said mechanical pressure means is a spring.

* * * * *